United States Patent
Mann et al.

(10) Patent No.: US 8,785,351 B2
(45) Date of Patent: *Jul. 22, 2014

(54) HERBICIDAL COMPOSITIONS CONTAINING BENTAZON AND ALS INHIBITOR AND ACCASE INHIBITOR

(71) Applicant: Dow AgroSciences LLC, Indianapolis, IN (US)

(72) Inventors: Richard K. Mann, Franklin, IN (US); Yi-hsiou Huang, Pingtung Hsieng (TW); Lap Nguyen, Hcm (VN)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/738,453

(22) Filed: Jan. 10, 2013

(65) Prior Publication Data

US 2013/0184156 A1   Jul. 18, 2013

Related U.S. Application Data

(60) Provisional application No. 61/585,844, filed on Jan. 12, 2012.

(51) Int. Cl.
*A01N 43/72* (2006.01)
*A01N 43/90* (2006.01)
*A01N 43/88* (2006.01)

(52) U.S. Cl.
CPC ............ *A01N 43/88* (2013.01); *A01N 43/90* (2013.01)
USPC .......................................... 504/132

(58) Field of Classification Search
None
See application file for complete search history.

(56) References Cited

U.S. PATENT DOCUMENTS

| | | |
|---|---|---|
| 2006/0183637 A1 | 8/2006 | Loughner et al. |
| 2006/0265780 A1 | 11/2006 | Prosch et al. |
| 2008/0194408 A1 | 8/2008 | Ramachandran et al. |
| 2009/0062121 A1* | 3/2009 | Satchivi et al. ............... 504/105 |
| 2010/0190794 A1* | 7/2010 | Hupe et al. .................... 514/245 |
| 2010/0322990 A1 | 12/2010 | Burke et al. |
| 2012/0015811 A1 | 1/2012 | Dave et al. |

* cited by examiner

*Primary Examiner* — Abigail Fisher
*Assistant Examiner* — Daniel L Branson
(74) *Attorney, Agent, or Firm* — Robert Chang

(57) ABSTRACT

Herbicidal compositions comprising (a) bentazon-sodium and (b) an ALS inhibitor and (c) an ACCase inhibitor controls susceptible and resistant weeds in crops, e.g., rice, wheat, barley, oats, rye, sorghum, corn/maize, pastures, grasslands, rangelands, fallowland, turf, tree and vine orchards and IVM, but also additionally in ALS and ACC'ase tolerant crops.

22 Claims, No Drawings

HERBICIDAL COMPOSITIONS CONTAINING BENTAZON AND ALS INHIBITOR AND ACCASE INHIBITOR

CROSS REFERENCE TO RELATED APPLICATIONS

This application claims the benefit of U.S. Provisional Patent Application Ser. No. 61/585,844, filed Jan. 12, 2012, the entirety of which is incorporated herein by reference.

FIELD

This disclosure concerns herbicidal compositions comprising and methods utilizing three herbicidal active ingredients, specifically (a) bentazon-sodium, (b) one ALS inhibitor and (c) one ACCase inhibitor for controlling weeds, including in crop settings, e.g., rice, wheat, barley, oats, rye, sorghum, corn/maize, pastures, grasslands, rangelands, fallowland, turf, tree and vine orchards and IVM, as well as ALS and ACCase tolerant crops (such as, but not limited to, soybean, cotton, canola/oilseed rape, rice, cereals, corn, turf, etc.). In some embodiments, these compositions provide improved post-emergence herbicidal weed control in rice.

BACKGROUND

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use.

In some cases, herbicidal active ingredients have been shown to be more effective in combination than when applied individually and this is referred to as "synergism." As described in the *Herbicide Handbook* of the Weed Science Society of America, Ninth Edition, 2007, p. 429 "'synergism' [is] an interaction of two or more factors such that the effect when combined is greater than the predicted effect based on the response to each factor applied separately." The present disclosure is based in part on the discovery that penoxsulam, cyhalofop-butyl and bentazon, already known individually for their herbicidal efficacy, display a synergistic effect when applied in a three-way combination.

SUMMARY

The present disclosure concerns herbicidal compositions comprising and methods utilizing herbicidally effective amounts of three herbicidal active ingredients, wherein the first herbicidal active ingredient is bentazon-sodium, the second herbicidal active ingredient an ALS inhibitor and the third herbicidal active ingredient an ACCase inhibitor. The compositions may also contain an agriculturally acceptable adjuvant and/or carrier.

The present disclosure also concerns herbicidal compositions for and methods of controlling the growth of undesirable vegetation, e.g., in monocot crops including rice, wheat, barley, oats, rye, sorghum, corn/maize, pastures, grasslands, rangelands, fallowland, turf, tree and vine orchards and IVM and, additionally, in ALS- and ACCase-tolerant crops (such as, but not limited to, soybean, cotton, canola/oilseed rape, rice, cereals, corn, turf, etc.).

DETAILED DESCRIPTION

Provided herein are herbicidal compositions comprising herbicidally effective amounts of three herbicidal active ingredients, wherein the first herbicidal active ingredient is bentazon-sodium, the second herbicidal active ingredient is an ALS inhibitor and the third herbicidal active ingredient is an ACCase inhibitor.

Provided herein are methods of controlling undesirable vegetation comprising applying herbicidally effective amounts of three herbicidal active ingredients, wherein the first herbicidal active ingredient is bentazon-sodium, the second herbicidal active ingredient is an ALS inhibitor and the third herbicidal active ingredient is an ACCase inhibitor.

Exemplary ALS inhibitors include, but are not limited to, penoxsulam, bispyribac-sodium, azimsulfuron, bensulfuron-methyl, chloransulam, cinosulfuron, diclosulam, ethoxysulfuron, flazasulfuron, florasulam, flumetsulam, halosulfuron-methyl, imazamox, imazethapyr, imazosulfuron, iofensulfuron, metazosulfuron, metsulfuron-methyl, orthosulfamuron, propyrisulfuron, pyrazosulfuron-ethyl, pyribenzoxim, pyriftalid, pyriminobac-methyl, pyrimisulfan, pyroxsulam and triafamone.

Exemplary ACCase inhibitors include, but are not limited to cyhalofop-butyl, fenoxaprop-P-ethyl, clodinafop-propyrgyl, diclofop-methyl, fluazifop-P-butyl, haloxyfop-methyl, propaquizafop, quizalofop-P-ethyl, clethodim, cycloxydim, profoxydim, sethoxydim, tepraloxydim, tralkoxydim and pinoxaden.

As used herein, penoxsulam is the common name for 2-(2,2-difluoroethoxy)-N-(5,8-dimethoxy[1,2,4]triazolo[1,5-c]pyrimidin-2-yl)-6-(trifluoromethyl)benzenesulfonamide and possesses the following structure:

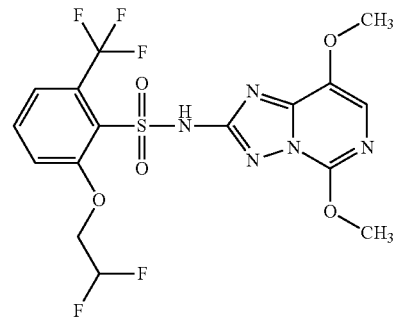 [SMILES: COc1cnc(OC)n2nc(NS(=O)(=O)c3c(OCC(F)F)cccc3C(F)(F)F)nc12]

Its herbicidal activity is exemplified in Tomlin, C., ed. A World Compendium The Pesticide Manual. 15$^{th}$ ed. Alton: BCPC Publications, 2009 (hereafter "*The Pesticide Manual*, Fifteenth Edition, 2009."). Exemplary uses of penoxsulam include, but are not limited to, the control of *Echinochloa* spp., as well as many broadleaf, sedge and aquatic weeds in rice, and *Apera* spp. grass in cereals, as well as many broadleaf weeds in aquatics, many cereal crops, range and pasture, IVM and turf.

As used herein, bispyribac-sodium is the common name for sodium 2,6-bis(4,6-dimethoxypyrimidin-2-yloxy)benzoate and possesses the following structure:

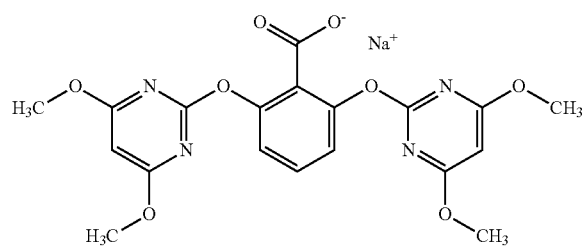

Its herbicidal activity is described in *The Pesticide Manual*, Fifteenth Edition, 2009. Exemplary uses of bispyribac-sodium include, but are not limited to, its use as a herbicide for the control of grasses, sedges and broad-leaved weeds. In one embodiment, bispyribac-sodium controls *Echinochloa* spp., in direct-seeded rice, and in another embodiment may also be used to stunt growth of weeds in non-crop situations.

Bentazon is the common name for 3-(1-methylethyl)-1H-2,1,3-benzothiadiazin-4(3H)-one 2,2-dioxide and possesses the following structure:

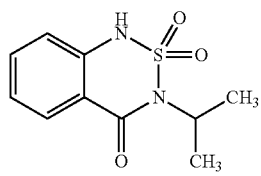 [SMILES: CC(C)N1C(=O)c2ccccc2NS1(=O)=O]

Its herbicidal activity is described in *The Pesticide Manual*, Fifteenth Edition, 2009. Exemplary uses of bentazon include, but are not limited to, its use as a herbicide for the control of a wide range of economically important broadleaf and sedge weeds. Bentazon is also known as bentazone and bendioxide. In certain embodiments, it can be used as the acid itself or as an agriculturally acceptable salt or ester. An exemplary bentazon salt is the sodium salt.

Cyhalofop-butyl is the common name for (R)-butyl 2-[4-(4-cyano-2-fluorophenoxy)phenoxy]propanoate and possesses the following structure:

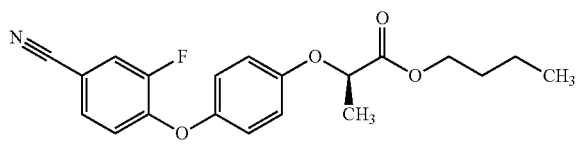 [SMILES: CCCCOC(=O)[C@@H](C)Oc1ccc(Oc2ccc(C#N)cc2F)cc1]

Its herbicidal activity is described in *The Pesticide Manual*, Fifteenth Edition, 2009. Exemplary uses of cyhalofop include, but are not limited to, its use as a herbicide for the post-emergence control of grass weeds in rice. It can be used as the acid itself or as an agriculturally acceptable salt or ester. An exemplary cyhalofop ester is the butyl ester.

Fenoxaprop-P-ethyl is the common name for (R)-ethyl-2-[4-(6-chloro-1,3-benzoxazol-2-yloxy)phenoxy]propanoate and possesses the structure:

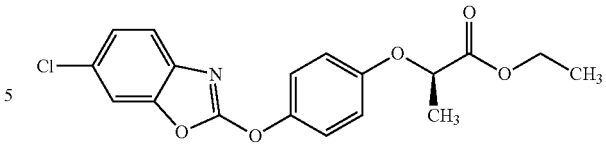

Its herbicidal activity is described in *The Pesticide Manual*, Fifteenth Edition, 2009. Exemplary uses of fenoxaprop include, but are not limited to, its use as a herbicide for the post emergence control of annual and perennial grass weeds in potatoes, beans, soya beans, beets, vegetables, peanuts, flax, oilseed rape and cotton; and (when applied with the herbicide safener mefenpyr-diethyl) annual and perennial grass weeds and wild oats in wheat, rye, triticale and, depending on ratio, in some varieties of barley. In some embodiments fenoxaprop is used as an ester, an exemplary ester being the P-ethyl ester.

The species spectra of bentazon-sodium, the ALS inhibitor and the ACCase inhibitor, i.e., the weed species which the respective compounds control, are broad and highly complementary. For example, it has been surprisingly found that a combination of penoxsulam plus cyhalofop-butyl plus bentazon-sodium salt exhibits a synergistic action in the control of barnyardgrass (*Echinochloa crus-galli*; ECHCG), Chinese sprangletop (*Leptochloa chinensis*, LEFCH), *monochoria* (*Monochoria vaginalis*, MOOVA), globe fringerush (*Fimbristylis miliacea*, FIMMI) and rice flatsedge (*Cyperus iria*; CYPIR) at application rates equal to or lower than the rates of the individual compounds. It has been surprisingly found that a combination of penoxsulam plus fenoxaprop-P-ethyl plus bentazon-sodium salt exhibits a synergistic action in the control of barnyardgrass (*Echinochloa crus-galli*; ECHCG) and *monochoria* (*Monochoria vaginalis*, MOOVA) at application rates equal to or lower than the rates of the individual compounds. It has been surprisingly found that a combination of bispyribac-sodium plus cyhalofop-butyl plus bentazon-sodium salt exhibits a synergistic action in the control of barnyardgrass (*Echinochloa crus-galli*; ECHCG) at application rates equal to or lower than the rates of the individual compounds.

The term herbicide or herbicidal active ingredient is used herein to mean an active ingredient that kills, controls or otherwise adversely modifies the growth of plants. A herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings, plants emerging from vegetative propagules, and established vegetation.

In some embodiments, the compositions and methods provided herein are utilized to control weeds in crops, including but not limited to rice, wheat, barley, oats, rye, sorghum, corn/maize, pastures, grasslands, rangelands, fallowland, turf, tree and vine orchards and IVM, rights-of-way and in any ALS or ACCase tolerant crops.

The compositions and methods described herein can be used to control undesirable vegetation in glyphosate-tolerant-, glufosinate-tolerant-, dicamba-tolerant-, phenoxy auxin-tolerant-, pyridyloxy auxin-tolerant-, aryloxyphenoxypropionate-tolerant-, acetyl CoA carboxylase (ACCase) inhibitor-tolerant-, imidazolinone-tolerant-, acetolactate synthase (ALS) inhibitor-tolerant-, 4-hydroxyphenyl-pyruvate dioxygenase (HPPD) inhibitor-tolerant-, protoporphyrinogen oxidase (PPO) inhibitor-tolerant-, triazine-tolerant- and bromoxynil-tolerant crops (such as, but not limited to, soybean, cotton, canola/oilseed rape, rice, cereals, corn, turf, etc), for example, in conjunction with glyphosate, glufosinate, dicamba, phenoxy auxins, pyridyloxy auxins, aryloxyphenoxypropionates, ACCase inhibitors, imidazolinones, ALS inhibitors, HPPD inhibitors, PPO inhibitors, triazines, and bromoxynil. The compositions and methods may be used in controlling undesirable vegetation in crops possessing multiple or stacked traits conferring tolerance to multiple chemistries and/or inhibitors of multiple modes of action. In some embodiments, penoxsulam plus cyhalofop-butyl plus bentazon-sodium, penoxsulam plus fenoxaprop-P-ethyl plus bentazon-sodium, and bispyribac-sodium plus cyhalofop-butyl plus bentazon-sodium, and other bentazon-sodium combinations plus 1 ALS inhibitor plus 1 ACCase inhibitor are used in combination with herbicides that are selective for the crop being treated and which complement the spectrum of weeds controlled by these compounds at the application rate employed. In some embodiments, the compositions described herein and other complementary herbicides are applied at the same time, either as a combination formulation, as a tank mix, or as a sequential application.

The compositions and methods provided herein are utilized to control undesirable vegetation. Undesirable vegetation includes, but is not limited to, undesirable vegetation that occurs rice, wheat, barley, oats, rye, sorghum, corn/maize, pastures, grasslands, rangelands, fallowland, turf, tree and vine orchards, IVM and rights-of-way.

In some embodiments, the methods provided herein are utilized to control undesirable vegetation in rice. In certain embodiments, the undesirable vegetation is *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) LINK (junglerice, ECHCO), *Echinochloa oryzoides* (Ard.) Fritsch (early watergrass, ECHOR), *Echinochloa oryzicola* (Vasinger) Vasinger (late watergrass, ECHPH), *Echinochloa* spp, *Ischaemum rugosum* Salisb. (saramollagrass, ISCRU), *Leptochloa chinensis* (L.) Nees (Chinese sprangletop, LEFCH), *Leptochloa fascicularis* (Lam.) Gray (bearded sprangletop, LEFFA), *Leptochloa panicoides* (Presl.) Hitchc. (Amazon sprangletop, LEFPA), *Panicum dichotomiflorum* (L.) Michx. (fall panicum, PANDI), *Paspalum dilatatum* Poir. (dallisgrass, PASDI), *Cyperus difformis* L. (smallflower flatsedge, CYPDI), *Cyperus esculentus* L. (yellow nutsedge, CYPES), *Cyperus iria* L. (rice flatsedge, CYPIR), *Cyperus rotundus* L. (purple nutsedge, CYPRO), *Eleocharis* species (ELOSS), *Fimbristylis miliacea* (L.) Vahl (globe fringerush, FIMMI), *Schoenoplectus juncoides* Roxb. (Japanese bulrush, SPCJU), *Schoenoplectus maritimus* L. (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago-aquatica* L. (common waterplantain, ALSPA), *Amaranthus* species, (pigweeds and amaranths, AMASS), *Ammannia coccinea* Rottb. (redstem, AMMCO), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea hederacea* (L.) Jacq. (ivyleaf morningglory, IPOHE), *Lindernia dubia* (L.) Pennell (low false pimpernel, LIDDU), *Monochoria korsakowii* Regel & Maack (monochoria, MOOKA), *Monochoria vaginalis* (Burm F.) C. Presl ex Kuhth, (monochoria, MOOVA), *Murdannia nudiflora* (L.) Brenan (doveweed, MUDNU), *Polygonum pensylvanicum* L., (Pennsylvania smartweed, POLPY), *Polygonum persicaria* L. (ladysthumb, POLPE), *Polygonum hydropiperoides* Michx. (POLHP, mild smartweed), *Rotala indica* (Willd.) Koehne (Indian toothcup, ROTIN), *Sagittaria* species, (arrowhead, SAGSS), *Sesbania exaltata* (Raf.) Cory/Rydb. Ex Hill (hemp sesbania, SEBEX), or *Sphenoclea zeylanica* Gaertn. (gooseweed, SPDZE).

In some embodiments, the methods provided herein are utilized to control undesirable vegetation found in tree and vine, perennial crops and row crops, including but not limited to vineyards, orchards, perennial plantation crops, corn, sorghum, sunflower, oilseed rape and vegetables. In certain embodiments, the undesirable vegetation is *Alopecurus myosuroides* Huds. (blackgrass, ALOMY), *Avena fatua* L. (wild oat, AVEFA), *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Lolium multiflorum* Lam. (Italian ryegrass, LOLMU), *Panicum dichotomiflorum* Michx. (fall panicum, PANDI), *Panicum miliaceum* L. (wild-proso millet, PANMI), *Setaria faberi* Herrm. (giant foxtail, SETFA), *Setaria viridis* (L.) Beauv. (green foxtail, SETVI), *Sorghum-halepense* (L.) Pers. (Johnsongrass, SORHA), *Sorghum bicolor* (L.) Moench ssp. *Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (western ragweed, AMBPS), *Ambrosia trifida* L. (giant ragweed, AMBTR), *Asclepias syriaca* L. (common milkweed, ASCSY), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Erigeron bonariensis* L. (hairy fleabane, ERIBO), *Erigeron canadensis* L. (Canadian fleabane, ERICA), *Helianthus annuus* L. (common sunflower, HELAN), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Sida spinosa* L. (prickly sida, SIDSP), *Sinapis arvensis* L. (wild mustard, SINAR), *Solanum ptychanthum* Dunal (eastern black nightshade, SOLPT), *Taraxacum officinale* F. H. Wigg (common dandelion, TAROF) or *Xanthium strumarium* L. (common cocklebur, XANST).

In some embodiments, the methods provided herein are utilized to control undesirable vegetation in cereals. In certain embodiments, the undesirable vegetation is *Alopecurus myosuroides* Huds. (blackgrass, ALOMY), *Apera spica-venti* (L.) Beauv. (windgrass, APESV), *Avena fatua* L. (wild oat, AVEFA), *Bromus tectorum* L. (downy brome, BROTE), *Lolium multiflorum* Lam. (Italian ryegrass, LOLMU), *Phalaris minor* Retz. (littleseed canarygrass, PHAMI), *Poa annua* L. (annual bluegrass, POANN), *Setaria pumila* (Poir.) Roemer & J. A. Schultes (yellow foxtail, SETLU), *Setaria viridis* (L.) Beauv. (green foxtail, SETVI), *Cirsium arvense* (L.) Scop. (Canada thistle, CIRAR), *Galium aparine* L. (catchweed bedstraw, GALAP), *Kochia scoparia* (L.) Schrad. (kochia, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Stellaria media* (L.) Vill. (common chickweed, STEME), *Veronica persica* Poir. (Persian speedwell, VERPE), *Viola arvensis* Murr. (field violet, VIOAR), or *Viola tricolor* L. (wild violet, VIOTR).

In some embodiments, the methods provided herein are utilized to control undesirable vegetation in range and pasture, IVM and rights of way. In certain embodiments, the undesirable vegetation is *Ambrosia artemisiifolia* L. (common ragweed, AMBEL), *Cassia obtusifolia* (sickle pod, CASOB), *Centaurea maculosa* auct. non Lam. (spotted knapweed, CENMA), *Cirsium arvense* (L.) Scop. (Canada thistle, CIRAR), *Convolvulus arvensis* L. (field bindweed, CONAR), *Euphorbia esula* L. (leafy spurge, EPHES), *Lactuca serriola* L./Torn. (prickly lettuce, LACSE), *Melochia parviflora* (escoba blanca, MEOPA), *Plantago lanceolata* L. (buckhorn plantain, PLALA), *Rumex obtusifolius* L. (broadleaf dock, RUMOB), *Sida spinosa* L. (prickly sida, SIDSP), *Sinapis arvensis* L. (wild mustard, SINAR), *Sonchus arvensis* L. (perennial sowthistle, SONAR), *Solidago* species (goldenrod, SOOSS), *Taraxacum officinale* G. H. Weber ex Wiggers (dandelion, TAROF), *Trifolium repens* L. (white clover, TRFRE), or *Urtica dioica* L. (common nettle, URTDI).

In some embodiments, the compositions and methods provided herein are utilized to control undesirable vegetation consisting of grass, broadleaf and sedge weeds. In certain embodiments, the compositions and methods provided herein are utilized to control undesirable vegetation including *Cyperus, Echinochloa, Fimbristylis, Leptochloa* and *Monochoria*.

In some embodiments, the methods utilize bentazon-sodium, penoxsulam, and cyhalofop-butyl, and the undesirable vegetation is *Cyperus, Echinochloa, Fimbristylis, Leptochloa*, or *Monochoria*. In some embodiments the undesirable vegetation is ECHCH, MOOVA, FIMMI, LEFCH, or CYPIR.

In some embodiments, the methods utilize bentazon-sodium, penoxsulam, and fenoxaprop-P-ethyl, and the undesirable vegetation is *Echinochloa* or *Monochoria*. In some embodiments the undesirable vegetation is ECHCH or MOOVA.

The methods employing the combination of penoxsulam plus cyhalofop-butyl plus bentazon-sodium, penoxsulam plus fenoxaprop-P-ethyl plus bentazon-sodium and bispyribac-sodium plus cyhalofop-butyl plus bentazon-sodium, or agriculturally acceptable salts or esters of any component, and the compositions described herein may also be employed to control herbicide resistant or tolerant weeds. Exemplary resistant or tolerant weeds include, but are not limited to, biotypes resistant or tolerant to acetolactate synthase (ALS) inhibitors, photosystem II inhibitors, acetyl CoA carboxylase (ACCase) inhibitors, synthetic auxins, photosystem I inhibitors, 5-enolpyruvylshikimate-3-phosphate (EPSP) synthase inhibitors, microtubule assembly inhibitors, lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, multiple chemical classes, and multiple herbicide modes-of-action.

In some embodiments, the compositions described herein are applied as a post-emergence foliar application to immature, undesirable vegetation to achieve the maximum control of weeds, or applied directly into water to immature, undesirable vegetation to achieve the maximum control of weeds.

Herbicidal activity is exhibited by the compounds when they are applied directly to the plant, to the locus of the plant at any stage of growth or before planting or emergence or after emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. In some embodiments, the compositions described herein are applied to relatively immature undesirable vegetation to achieve the maximum control of weeds.

In some embodiments, the compositions comprise and methods utilize bentazon-sodium, penoxsulam, and cyhalofop-butyl. In some embodiments, the weight ratio of (a) bentazon-sodium to (b) penoxsulam to (c) cyhalofop-butyl is (a) 50-150 to (b) 0.5-1.5 to (c) 4-40. In another embodiment, the weight ratio is (a) 70-90 to (b) 1 to (c) 8-23.

In some embodiments, the compositions comprise and methods utilize bentazon-sodium, penoxsulam, and fenoxaprop-P-ethyl. In some embodiments, the weight ratio of (a) bentazon-sodium to (b) penoxsulam to (c) fenoxaprop-P-ethyl is (a) 50-100 to (b) 0.5-1.5 to (c) 0.5-1.5. In another embodiment, the weight ratio is (a) 75 to (b) 1 to (c) 1.

In some embodiments, the compositions comprise and methods utilize bentazon-sodium, bispyribac-sodium, and cyhalofop-butyl. In some embodiments, the weight ratio of (a) bentazon-sodium to (b) bispyribac-sodium to (c) cyhalofop-butyl is (a) 25 to 75 (b) 0.5-1.5 to (c) 10-20. In another embodiment, the weight ratio is (a) 56 to (b) 1 to (c) 19.

The rate at which the composition is applied will depend upon the particular type of weed to be controlled, the degree of control required, and the timing and method of application. In general, the compositions of the disclosure can be applied at an application rate from about 113 grams active ingredient per hectare (g ai/ha) to about 2575 g ai/ha based on the total amount of active ingredients in the composition. In another embodiment, the compositions of the disclosure can be applied at an application rate from about 150 grams active ingredient per hectare (g ai/ha) to about 245 g ai/ha based on the total amount of active ingredients in the composition. Penoxsulam is applied at a rate from about 1 g ai/ha to about 50 g ai/ha, bispyribac-sodium is applied at a rate from about 4 g aiha to about 75 g ai/ha, bentazon-sodium is applied at a rate from about 112 g ai/ha to about 2000 g ai/ha, cyhalofop-butyl is applied at a rate from about 37 g ai/ha to 500 g ai/ha and fenoxaprop-P-ethyl is applied at a rate from about 8 g ai/ha to 500 g ai/ha.

The components of the mixtures described herein can be applied either separately or as part of a multipart herbicidal system.

The mixtures of the present disclosure can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the synergistic composition described herein include: 2,4-D esters & amines, acetochlor, acifluorfen, aclonifen, AE0172747, alachlor, amidosulfuron, aminocyclopyrachlor, aminopyralid, aminotriazole, ammonium thiocyanate, anilifos, atrazine, azimsulfuron, benfuresate, bensulfuron-methyl, benthiocarb, benzobicyclon, benzofenap, bifenox, bispyribac-sodium, bromacil, bromobutide, bromoxynil, butachlor, butafenacil, butralin, cafenstrole, carbetamide, carfentrazone-ethyl, chlorflurenol, chlorimuron, chlorpropham, cinosulfuron, clethodim, clodinafop-propargyl, clomazone, clomeprop, clopyralid, cloransulam-methyl, cyclosulfamuron, cycloxydim, daimuron, dicamba, dichlobenil, dichlorprop-P, diclosulam, diflufenican, diflufenzopyr, dimepiperate, dimethenamid, dimethenamid-p, diquat, dithiopyr, diuron, EK2612, EPTC, esprocarb, ET-751, ethoxysulfuron, etobenzanid, fenoxaprop, fenoxaprop-P-ethyl, fenoxaprop-ethyl+isoxadifen-ethyl, fentrazamide, flazasulfuron, florasulam, fluazifop, fluazifop-P-butyl, flucetosulfuron (LGC-42153), flufenacet, flufenpyr-ethyl, flumetsulam, flumiclorac-pentyl, flumioxazin, fluometuron, flupyrsulfuron, fluoroxypyr, fluoroxypyr-meptyl heptyl ester (MHE), fomesafen, foramsulfuron, fumiclorac, glufosinate, glufosinate-ammonium, glyphosate, halosulfuron, haloxyfop-methyl, haloxyfop-P-methyl, imazamethabenz, imazamox, imazapic, imazapyr, imazaquin, imazethapyr, imazosulfuron, indanofan, indaziflam, iodosulfuron, ioxynil, ipfencarbazone (HOK-201), IR 5790, isoproturon, isoxaben, isoxaflutole, KUH-071, lactofen, linuron, iofensulfuron, MCPA, MCPA ester & amine, MCPB, MCPB ester & amine, mecoprop-P, mefenacet, mesosulfuron, mesotrione, metamifop, metazosulfuron (NC-620), metolachlor, metosulam, metribuzin, metsulfuron, molinate, MSMA, napropamide, nicosulfuron, norflurazon, OK-9701, orthosulfamuron, oryzalin, oxadiargyl, oxadiazon, oxazichlomefone, oxyfluorfen, paraquat, pendimethalin, pentoxazone, pethoxamid, picloram, picolinafen, pinoxaden, piperophos, pretilachlor, primisulfuron, profoxydim, propachlor, propanil, propyrisulfuron, propyzamide, prosulfocarb, prosulfuron, pyraclonil, pyrazolynate, pyrazosulfuron, pyribenzoxim (LGC-40863), pyributicarb, pyridate, pyriftalid, pyriminobac-methyl, pyrimisulfan (KUH-021), pyroxasulfone (KIH-485), pyroxsulam, quinclorac, quizalofop-P-ethyl, S-3252, saflufenacil, sethoxydim, simazine, SL-0401, SL-0402, S-metolachlor, sulcotrione, sulfentrazone, sulfosate, tebuthiuron, tefuryltrione (AVH-301), terbacil, thenylchlor, thiazopyr, thiobencarb, tralkoxydim, triafamone, triclopyr, triclopyr-esters and amines, trifluralin, tritosulfuron, DE-729 (halauxifen-methyl) esters and amines and benzyl 4-amino-3-chloro-6-(4-chloro-2-fluoro-3-methoxyphenyl)-5-fluoropicolinate esters and amines.

The compositions of the present disclosure can, further, be used in conjunction with glyphosate, glufosinate, dicamba, imidazolinones, sulfonylureas, ACCase (aryloxyphenoxyproprionate and cyclohexanediones) or 2,4-D on glyphosate-tolerant, glufosinate-tolerant, dicamba-tolerant, imidazolinone-tolerant, sulfonylurea-tolerant, ACCase tolerant and 2,4-D-tolerant crops. In some embodiments, the compositions described herein are used in combination with herbicides that are selective for the crop being treated and which complement the spectrum of weeds controlled by these compounds at the application rate employed. In other embodiments, the compositions of the present disclosure and other complementary herbicides are applied at the same time, either as a combination formulation or as a tank-mix.

The compositions of the present disclosure can be employed in combination with known herbicide safeners, such as benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, isoxadifen-ethyl, mefenpyr-diethyl, MG 191, MON 4660, naphthalic anhydride (NA), oxabetrinil, R29148 and N-phenyl-sulfonylbenzoic acid amides, to enhance their selectivity.

In practice, the compositions described herein are used in mixtures containing a herbicidally effective amount of the herbicidal components along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures described herein are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. In some embodiments, water is used for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

In some embodiments, it is desirable to incorporate one or more surface-active agents into the compositions of the present disclosure. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzene-sulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils.

Other additives commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

In some embodiments, the concentration of the active ingredients in the synergistic composition of the present disclosure is from 0.1 to 98 percent by weight, and in other embodiments, concentrations from 10 to 90 percent by weight are employed. In certain embodiments in which the compositions are designed to be employed as concentrates, the active ingredients may be present in a concentration from about 5 to about 98 weight percent, and in other embodiments from about 10 to about 90 weight percent. Such compositions may be diluted with an inert carrier, such as water, before making a postemergence, foliar application to exposed weed and crop foliage, or may be applied as a dry or liquid formulation directly into flooded rice fields or other aquatic conditions. In some embodiments the diluted compositions are applied as a postemergence, foliar application to weeds or the locus of weeds and contain from about 0.02 to about 20 weight percent active ingredient and in other embodiments contain from about 0.04 to about 10 weight percent active ingredient.

The present compositions can be applied to weeds or their locus by the use of conventional ground or aerial dusters, sprayers, and granule applicators, by addition to irrigation or paddy water, and by other conventional means known to those skilled in the art.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

Evaluation of Postemergence Herbicidal Activity of Mixtures in the Field

Field trials were conducted in Vietnam and Taiwan in cultivated direct-seeded rice using standard herbicide small plot research methodology. Plots varied from 1×2 meter (m) to 4×5 m (width×length) with 3-4 replicates per treatment. The rice crop was grown using normal cultural practices for fertilization, seeding, watering, flooding and maintenance to ensure good growth of the crop and the weeds.

All treatments in the field trials were applied using a backpack air sprayer with flat fan nozzles calibrated to apply 320 to 450 L/ha spray volume at approximately 30 PSI. Commercially available products of penoxsulam (Clipper 25OD), bispyribac-sodium (Nominee 100SC), bentazon-sodium (Basagran 480SL), cyhalofop-butyl (Clincher 100EC), and fenoxaprop-P-ethyl (Whip S) were mixed in water at appropriate formulated product rates to achieve the desired rates based on a unit area of application (hectare) to achieve the desired rates as shown. Treatments were rated at 7 to 42 days after application (DAA) as compared to the untreated control plants. Visual weed control was scored on a scale of 0 to 100 percent where 0 corresponds to no injury and 100 corresponds to complete kill.

Tables 1 to 5 demonstrate the herbicidal synergistic efficacy of bentazon-sodium mixes with one ALS inhibitor+one ACCase inhibitor tank mixes on weed control. All treatment results, both for the single product and mixtures, are an average of 3 to 4 replicates and the tank mix interactions are significant at the P>0.05 level.

Colby's equation was used to determine the herbicidal effects expected from the mixtures (Colby, S. R. Calculation of the synergistic and antagonistic response of herbicide combinations. *Weeds* 1967, 15, 20-22.).

The following equation was used to calculate the expected activity of mixtures containing two active ingredients, A and B:

$$\text{Expected} = A+B+C-(AB+AC+BC)/100+(ABC)/10{,}000$$

A=observed efficacy of active ingredient A at the same concentration as used in the mixture.

B=observed efficacy of active ingredient B at the same concentration as used in the mixture.

C=observed efficacy of active ingredient C at the same concentration as used in the mixture.

Some of the compounds tested, application rates employed, plant species tested, and results are given in Tables 1-5. All comparisons are an average of 3 to 4 replicates and are significant at the P>0.05 level.

TABLE 1

Synergistic weed control of ECHCG following a postemergence application of Penoxsulam + Bentazon-Na + Cyhalofop-Butyl to rice in field trials.

| Penox-sulam | Bent-azon (Na) | Cyhalo-fop (Butyl) | % Visual Control | | | | | |
|---|---|---|---|---|---|---|---|---|
| | | | ECHCG (7 DAA) | | ECHCG (14 DAA) | | ECHCG (28 DAA) | |
| (grams ai/ha) | | | Obs | Exp | Obs | Exp | Obs | Exp |
| 5 | 0 | 0 | — | — | — | — | — | — |
| 0 | 450 | 0 | — | — | — | — | — | — |
| 0 | 0 | 37.5 | — | — | — | — | — | — |
| 5 | 450 | 37.5 | — | — | — | — | — | — |
| 10 | 0 | 0 | 58 | — | 60 | — | 60 | — |
| 0 | 900 | 0 | 0 | — | 0 | — | 0 | — |
| 0 | 0 | 75 | 37 | — | 43 | — | 40 | — |
| 10 | 900 | 75 | 90 | 74 | 93 | 77 | 88 | 76 |

ECHCG = *Echinochloa crus-galli*, barnyardgrass
DAA = Days after application
ai/ha = Active ingredient per hectare
Obs = Observed percent (%) average weed control
Exp = Expected percent (%) average weed control as predicted by Colby's Equation

TABLE 2

Synergistic weed control of MOOVA and FIMMI following a postemergence application of Penoxsulam + Bentazon-Na + Cyhalofop-Butyl to rice in field trials.

| Penox-sulam | Bent-azon (Na) | Cyhalo-fop (Butyl) | % Visual Control | | | | | |
|---|---|---|---|---|---|---|---|---|
| | | | MOOVA (7 DAA) | | MOOVA (14 DAA) | | FIMMI (42 DAA) | |
| (grams ai/ha) | | | Obs | Exp | Obs | Exp | Obs | Exp |
| 5 | 0 | 0 | 77 | — | 87 | — | — | — |
| 0 | 450 | 0 | 0 | — | 0 | — | — | — |
| 0 | 0 | 37.5 | 0 | — | 0 | — | — | — |
| 5 | 450 | 37.5 | 87 | 77 | 90 | 87 | — | — |
| 10 | 0 | 0 | — | — | — | — | 78 | — |
| 0 | 900 | 0 | — | — | — | — | 0 | — |
| 0 | 0 | 75 | — | — | — | — | 60 | — |
| 10 | 900 | 75 | — | — | — | — | 100 | 91 |

MOOVA = *Monochoria vaginalis*, monochoria
FIMMI = *Fimbristylis miliacea*, globe fringerush
DAA = Days after application
ai/ha = Active ingredient per hectare
Obs = Observed percent (%) average weed control
Exp = Expected percent (%) average weed control as predicted by Colby's Equation

TABLE 3

Synergistic weed control of LEFCH and CYPIR following a postemergence application of Penoxsulam + Bentazon-Na + Cyhalofop-Butyl to rice in field trials..

| Penoxsulam | Bentazon (Na) | Cyhalofop (Butyl) | % Visual Control | | | |
|---|---|---|---|---|---|---|
| | | | LEFCH (7 DAA) | | CYPIR (42 DAA) | |
| (grams ai/ha) | | | Obs | Exp | Obs | Exp |
| 1 | 0 | 0 | — | — | 75 | — |
| 0 | 112.5 | 0 | — | — | 63 | — |
| 0 | 0 | 9.4 | — | — | 0 | — |
| 1 | 112.5 | 9.4 | — | — | 100 | 90 |
| 1.6 | 0 | 0 | 0 | — | — | — |
| 0 | 112.5 | 0 | 0 | — | — | — |
| 0 | 0 | 37.5 | 83 | — | — | — |
| 1.6 | 112.5 | 37.5 | 99 | 83 | — | — |

LEFCH = *Leptochloa chinensis*, Chinese sprangletop
CYPIR = *Cyperus iria*, rice flatsedge
DAA = Days after application
ai/ha = Active ingredient per hectare
Obs = Observed percent (%) average weed control
Exp = Expected percent (%) average weed control as predicted by Colby's Equation

TABLE 4

Synergistic weed control of ECHCG and MOOVA following a postemergence application of Penoxsulam + Bentazon-Na + Fenoxaprop-P-Ethyl to rice in field trials.

| Penoxsulam | Bentazon (Na) | Fenoxaprop-P (Ethyl) | % Visual Control | | | |
|---|---|---|---|---|---|---|
| | | | ECHCG (7 DAA) | | MOOVA (7 DAA) | |
| (grams ai/ha) | | | Obs | Exp | Obs | Exp |
| 4 | 0 | 0 | 61 | — | 22 | — |
| 0 | 450 | 0 | 0 | — | 17 | — |
| 0 | 0 | 8 | 0 | — | 0 | — |
| 6 | 450 | 8 | 67 | 61 | 87 | 35 |

ECHCG = *Echinochloa crus-galli*, barnyardgrass
MOOVA = *Monochoria vaginalis*, monochoria
DAA = Days after application
ai/ha = Active ingredient per hectare
Obs = Observed percent (%) average weed control
Exp = Expected percent (%) average weed control as predicted by Colby's Equation

TABLE 5

Synergistic weed control of ECHCG following a postemergence application of Bispyribac-Na + Bentazon-Na + Cyhalofop-Butyl to rice in field trials.

| Bispyribac (Na) | Bentazon (Na) | Cyhalofop (Butyl) | % Visual Control ECHCG (14 DAA) | |
|---|---|---|---|---|
| (grams ai/ha) | | | Obs | Exp |
| 4 | 0 | 0 | 0 | — |
| 0 | 225 | 0 | 0 | — |
| 0 | 0 | 75 | 40 | — |
| 4 | 225 | 75 | 73 | 40 |

ECHCG = *Echinochloa crus-galli*, barnyardgrass
DAA = Days after application
ai/ha = Active ingredient per hectare
Obs = Observed percent (%) average weed control
Exp = Expected percent (%) average weed control as predicted by Colby's Equation

What is claimed is:

1. A syngergistic herbicidal composition comprising three herbicidal active ingredients, wherein the herbicidal active ingredients consist of bentazon-sodium, an ALS inhibitor, and an ACCase inhibitor.

2. The composition of claim 1, wherein the ALS inhibitor is penoxsulam, bispyribac-sodium, azimsulfuron, bensulfuron-methyl, chloransulam, cinosulfuron, diclosulam, ethoxysulfuron, flazasulfuron, florasulam, flumetsulam, halosulfuron-methyl, imazamox, imazethapyr, imazosulfuron, iofensulfuron, metazosulfuron, metsulfuron-methyl, orthosulfamuron, propyrisulfuron, pyrazosulfuron-ethyl, pyribenzoxim, pyriftalid, pyriminobac-methyl, pyrimisulfan, pyroxsulam or triafamone.

3. The composition of claim 1, wherein the ACCase inhibitor is cyhalofop-butyl, fenoxaprop-P-ethyl, clodinafop-propyrgyl, diclofop-methyl, fluazifop-P-butyl, haloxyfop-methyl, propaquizafop, quizalofop-P-ethyl, clethodim, cycloxydim, profoxydim, sethoxydim, tepraloxydim, tralkoxydim or pinoxaden.

4. The composition of claim 1, wherein the ALS inhibitor is penoxsulam and the ACCase inhibitor is cyhalofop butyl.

5. The composition of claim 4, wherein the weight ratio of (a) bentazon-sodium to (b) penoxsulam to (c) cyhalofop-butyl is (a) 50-150 to (b) 0.5-1.5 to (c) 4-40.

6. The composition of claim 4, wherein the weight ratio of (a) bentazon-sodium to (b) penoxsulam to (c) cyhalofop-butyl is (a) 70-90 to (b) 1 to (c) 8-23.

7. The composition of claim 1, wherein the ALS inhibitor is penoxsulam and the ACCase inhibitor is fenoxaprop-P-ethyl.

8. The composition of claim 7, wherein the weight ratio of (a) bentazon-sodium to (b) penoxsulam to (c) fenoxaprop-P-ethyl is (a) 50-100 to (b) 0.5-1.5 to (c) 0.5-1.5.

9. The composition of claim 7, wherein the weight ratio of (a) bentazon-sodium to (b) penoxsulam to (c) fenoxaprop-P-ethyl is (a) 75 to (b) 1 to (c) 1.

10. The composition of claim 1, wherein the ALS inhibitor is bispyribac-sodium and the ACCase inhibitor is cyhalofop-butyl.

11. The composition of claim 10, wherein the weight ratio of (a) bentazon-sodium to (b) bispyribac-sodium to (c) cyhalofop-butyl is (a) 25-75 to (b) 0.5-1.5 to (c) 10-20.

12. The composition of claim 10, wherein the weight ratio of (a) bentazon-sodium to (b) bispyribac-sodium to (c) cyhalofop-butyl is (a) 56 to (b) 1 to (c) 19.

13. The composition of claim 1, further comprising an agriculturally acceptable adjuvant or carrier.

14. A method of controlling undesirable vegetation comprising contacting the vegetation or the locus thereof with or applying to soil or water to prevent the emergence or growth of vegetation a herbicidally effective amount of the composition of claim 1.

15. A method of controlling undesirable vegetation comprising contacting the vegetation or the locus thereof with or applying to the soil or water to prevent the emergence or growth of vegetation a herbicidally effective amount of three herbicidal active ingredients, wherein the herbicidal active ingredients consist of bentazon-sodium, an ALS inhibitor, and an ACCase inhibitor.

16. The method of claim 15, wherein:
(a) the ALS inhibitor is penoxsulam, bispyribac-sodium, azimsulfuron, bensulfuron-methyl, chloransulam, cinosulfuron, diclosulam, ethoxysulfuron, flazasulfuron, florasulam, flumetsulam, halosulfuron-methyl, imazamox, imazethapyr, imazosulfuron, iofensulfuron, metazosulfuron, metsulfuron-methyl, orthosulfamuron, propyrisulfuron, pyrazosulfuron-ethyl, pyribenzoxim, pyriftalid, pyriminobac-methyl, pyrimisulfan, pyroxsulam or triafamone; and
(b) the ACCase inhibitor is cyhalofop-butyl, fenoxaprop-P-ethyl, clodinafop-propyrgyl, diclofop-methyl, fluazifop-P-butyl, haloxyfop-methyl, propaquizafop, quizalofop-P-ethyl, clethodim, cycloxydim, profoxydim, sethoxydim, tepraloxydim, tralkoxydim or pinoxaden.

17. The method of claim 15, wherein the ALS inhibitor is penoxsulam or bispyribac-sodium and the ACCase inhibitor is cyhalofop-butyl or fenoxaprop-P-ethyl.

18. The method of claim 15, wherein the ALS inhibitor is penoxsulam and the ACCase inhibitor is cyhalofop butyl.

19. The method of claim 15, wherein the ALS inhibitor is penoxsulam and the ACCase inhibitor is fenoxaprop-P-ethyl.

20. The method of claim 15, wherein the ALS inhibitor is bispyribac-sodium and the ACCase inhibitor is cyhalofop-butyl.

21. The method of claim 15, wherein the undesirable vegetation is controlled in the presence of rice crops.

22. A synergistic herbicidal composition comprising three herbicidal active ingredients, wherein the herbicidal active ingredients consist of bentazon-sodium, an ALS inhibitor, and an ACCase inhibitor, wherein
(a) the ALS inhibitor is penoxsulam and the ACCase inhibitor is cyhalofop butyl, and the weight ratio of bentazon-sodium:penoxsulam:cyhalofop-butyl is 70-90:1:8-23;
(b) the ALS inhibitor is penoxsulam, the ACCase inhibitor is fenoxaprop-P-ethyl, and the weight ratio of bentazon-sodium:penoxsulam:fenoxaprop-P-ethyl is 75:1:1; or
(c) the ALS inhibitor is bispyribac-sodium, the ACCase inhibitor is cyhalofop-butyl, and the weight ratio of bentazon-sodium:bispyribac-sodium:cyhalofop-butyl is 56:1:19.

* * * * *